US006495161B1

(12) United States Patent
Soon-Shiong et al.

(10) Patent No.: US 6,495,161 B1
(45) Date of Patent: Dec. 17, 2002

(54) CYTOPROTECTIVE BIOCOMPATIBLE CONTAINMENT SYSTEMS FOR BIOLOGICALLY ACTIVE MATERIALS AND METHODS OF MAKING SAME

(75) Inventors: Patrick Soon-Shiong, Malibu; Neil Desai, Los Angeles; Nilesh Ron, Culver City; Andrew Sojomihardjo S., West Covina; Roswitha Heintz, Los Angeles; Francesco Curcio, Westlake Village, all of CA (US)

(73) Assignee: VivoRx, Inc., Santa Monica, CA (US)

( * ) Notice: Subject to any disclaimer, the term of this patent is extended or adjusted under 35 U.S.C. 154(b) by 0 days.

(21) Appl. No.: 09/264,187

(22) Filed: Mar. 9, 1999

(51) Int. Cl.$^7$ ................................................. A61K 9/48
(52) U.S. Cl. ........................................ 424/451; 424/450
(58) Field of Search ................................. 424/450, 451, 424/489, 455, 456, 459, 460, 463, 461, 462, 484

(56) References Cited

U.S. PATENT DOCUMENTS 4,352,883 A  *  10/1982  Lim .......................... 435/178
5,545,423 A  *  8/1996  Soon-Shiong et al. ...... 424/484
5,700,848 A      12/1997  Soon-Shiong et al. ......... 522/7
5,759,578 A  *  6/1998  Soon-Shiong et al. ...... 424/484
5,788,988 A  *  8/1998  Soon-Shiong et al. ...... 424/484

OTHER PUBLICATIONS

Lim and Sun, "Microencapsulated Islets as Bioartificial Endocrine Pancreas," *Science,* 210:908–910 (1980).

* cited by examiner

*Primary Examiner*—Dameron L. Jones
(74) *Attorney, Agent, or Firm*—Stephen E. Reiter; Foley & Lardner

(57) ABSTRACT

In accordance with the invention, there are provided methods, capsules, and delivery systems useful in preparing biological containment systems with properties (e.g., mechanical strength, capsule permeability and porosity, desired controlled release rates of the biologic or components secreted by the biologic, and immunoreactivity) that can be varied to adapt to a broader range of physiological conditions than known biological containment systems. There are also provided methods of making capsules containing cell aggregates therein, as well as the capsules formed thereby, which are useful as a quantitatively plentiful and low cost alternative to usage of freshly harvested cell aggregates (e.g., islets from pancreas), since the latter are usually available only in limited numbers.

26 Claims, No Drawings

CYTOPROTECTIVE BIOCOMPATIBLE CONTAINMENT SYSTEMS FOR BIOLOGICALLY ACTIVE MATERIALS AND METHODS OF MAKING SAME

FIELD OF THE INVENTION

The present invention relates to new forms of biocompatible containment systems that envelop encapsulated or free cells or other biologically active materials. In a particular aspect, the present invention relates to a system that provides an immune barrier for the cells or other biologically active materials. In another aspect, the present invention relates to a system that provides enhanced migration and aggregation of the cells or other biologically active materials within the containment system. In a further aspect, the present invention relates to a system that provides enhanced transfer of the secretions of cells or other biologically active materials out of the containment system.

BACKGROUND OF THE INVENTION

Microencapsulation of cells (e.g., pancreatic islets) by an alginate-PLL-alginate membrane (i.e., an alginate-poly-L-lysine-alginate membrane) is a potential method for prevention of rejection of foreign cells by the host's immune system. By this technique, researchers are able to encapsulate living islets in a protective membrane that allows insulin to be secreted, yet prevents antibodies from reaching the islets, causing rejection of the cells. This membrane (or microcapsule) protects the islet from rejection and allows insulin to be secreted through its "pores" to maintain the diabetic in normal glucose control.

Successful transplants of microencapsulated cells have not been clinically feasible to date due to fundamental problems of transplant rejection and/or fibrotic reaction to the microcapsule. In the treatment of diabetes, Lim and Sun, 1980; Science 210:908, reported the first successful implantation of microencapsulated islets and described normalization of blood sugar in diabetic rats.

However, for microencapsulated cells to be clinically useful and applicable in humans, it is important that the capsule be biocompatible, allow adequate diffusion for the encapsulated cells to respond appropriately to a stimulatory signal and to provide the encapsulated cells with necessary nutrients, and optionally be retrievable. Retrievability is desirable for a variety of reasons, e.g., so that accumulation of the implanted materials can be avoided, so that encapsulated cells can be removed from the recipient when no longer needed or desired (e.g., when the product(s) of the encapsulated cells are no longer needed, if the encapsulated cells fail to perform as desired, etc.), so that encapsulated cells can be removed if/when they become non-viable, and the like.

Biocompatibility of encapsulated islets remains a fundamental problem. The term "biocompatible" is used herein in its broad sense, and relates to the ability of the material to result in long-term in vivo function of transplanted biological material, as well as its ability to avoid a foreign body, fibrotic response. A major problem with microencapsulation technology has been the occurrence of fibrous overgrowth of the epicapsular surface, resulting in cell death and early graft failure. Despite extensive studies, the pathological basis of this phenomenon in alginate based capsules remains poorly understood. However, several factors have recently been identified as being involved in graft failure, e.g., the guluronic acid/mannuronic acid content of the alginate employed, imperfections in the microcapsule membrane (allowing exposure of poly-L-lysine to the in vivo environment), failure of the microcapsule membrane to completely cover the cells being encapsulated (thereby allowing exposure of the cells to the in vivo environment), and the like.

Accordingly, there is a need in the art for new and better capsules for the encapsulation of biologically active materials. In addition, there is a need for new methods of making capsules that encapsulate biologically active materials while permitting variation of certain properties (e.g., mechanical strength, capsule permeability and porosity, desired controlled release rates of the biologic or components secreted by the biologic, and immunoreactivity) across broad performance ranges to address variable physiological conditions. Further, there is a need for new methods of facilitating formation of and delivery systems for cell aggregates.

BRIEF DESCRIPTION OF THE INVENTION

In accordance with the present invention, capsules (e.g., microcapsules and macrocapsules) have been developed for the encapsulation of biologically active materials therein. Invention capsules comprise at least one biocompatible gellable material, wherein at least the outer layer of the capsule is covalently crosslinked and optionally polyionically crosslinked (or, in the case of macrocapsules comprising microcapsules therein, either polyionically crosslinked, covalently crosslinked, or both polyionically crosslinked and covalently crosslinked), but not ionically crosslinked. Surprisingly, invention capsules permit enhanced migration and aggregation of the biologically active material within the capsule and enhanced control over the release rates of the biologically active material or components secreted by the biologically active material, while decreasing the risk of biomineralization due to ions required for ionic crosslinking and enabling the biologically active material contained within the capsule to retain a significant proportion of the functionality of the unencapsulated biologically active material.

In a further aspect of the present invention, there also have been developed methods of making invention capsules. One of the invention methods comprises subjecting a capsule whose outer layer is ionically crosslinked and covalently crosslinked, and optionally polyionically crosslinked (or, in the case of macrocapsules comprising microcapsules therein, ionically crosslinked and either polyionically crosslinked, covalently crosslinked, or both polyionically crosslinked and covalently crosslinked), to conditions sufficient to disrupt ionic crosslinking in at least the outer layer thereof. Surprisingly, invention methods facilitate the relatively rapid formation of invention capsules under conditions which are not cytotoxic, while decreasing the risk of biomineralization caused by the presence of ions required for ionic crosslinking and enabling the biologically active material contained within the capsule to retain a significant proportion of the functionality of the unencapsulated biologically active material.

Additional methods of making invention capsules comprise simultaneously subjecting a droplet comprising a suspension of biologically active materials in a covalently crosslinkable carrier to conditions sufficient to prevent substantial dissociation thereof and subjecting the droplet to conditions sufficient to induce substantial covalent crosslinking thereof. Surprisingly, these invention methods facilitate the relatively rapid formation of invention capsules under conditions which are not cytotoxic, while reducing to substantially zero the risk of biomineralization caused by the presence of ions required for ionic crosslinking and while enabling the biologically active material contained within the capsule to retain a significant proportion of the functionality of the unencapsulated biologically active material.

In a further aspect of the present invention, there also have been developed capsules containing cell aggregates therein, and methods for the production thereof. Invention capsules comprise a biocompatible gellable material, and have a core which is not ionically crosslinked, and at least an outer layer thereof which is covalently crosslinked, polyionically crosslinked, or both covalently crosslinked and polyionically crosslinked. Surprisingly, invention capsules permit enhanced migration and aggregation of the cell aggregates and constituent cells within the capsule and enhanced control over the release rates of the components secreted by the cell aggregates, while decreasing the risk of biomineralization due to ions required for ionic crosslinking and enabling the cell aggregates contained within the capsule to retain a significant proportion of the functionality of the unencapsulated cell aggregates.

Invention methods of making capsules containing cell aggregates therein described herein comprise subjecting a capsule, comprising a biocompatible gellable material and having a core which is ionically crosslinked, to conditions sufficient to disrupt ionic crosslinking therein. Surprisingly, invention methods facilitate enhanced migration and aggregation of the cell aggregates and their constituent components within the capsule and enhanced control over the release rates of the biologically active material or of the components secreted by the biologically active material, while decreasing the risk of biomineralization due to ions required for ionic crosslinking and facilitating the ability of the cell aggregates contained within the capsule to retain a significant proportion of the functionality of the unencapsulated cell aggregates.

In an additional aspect of the present invention, there also have been developed delivery systems comprising the invention capsules. Surprisingly, invention delivery systems permit enhanced diffusion, across and throughout the capsule, of the biologically active material contained therein, or of the compound secreted by the biologically active material contained therein, or of the compound to be catalyzed and/or reacted by the biologically active material contained therein, while decreasing the risk of biomineralization due to ions required for ionic crosslinking and enabling the biologically active material contained within the capsule to retain a significant proportion of the functionality of the unencapsulated biologically active material.

The present invention provides many advantages over the art. For example, invention methods, capsules, and delivery systems are useful in preparing biological containment systems with properties (e.g., mechanical strength, capsule permeability and porosity, desired controlled release rates of the biologic or components secreted by the biologic, and immunoreactivity) that can be varied to adapt to a broader range of physiological conditions. This variation and adaptability are due to the broader range of ratios of ionic to covalent linkages in the biocompatible gellable material permitted by the present invention. Further, invention methods of making capsules containing cell aggregates therein, as well as the capsules formed thereby, are useful as a quantitatively plentiful and low cost alternative to usage of freshly harvested cell aggregates (e.g., islets from pancreas), since the latter are usually available only in limited numbers. Other advantages of the present invention can be readily recognized by those of ordinary skill in the art upon inspection of the detailed description and appended claims provided herewith.

DETAILED DESCRIPTION OF THE INVENTION

In accordance with the present invention, there are provided microcapsules containing biologically active materials therein. Invention microcapsules comprise an ionically crosslinkable biocompatible gellable material, wherein at least the outer layer of said microcapsule is covalently crosslinked and optionally polyionically crosslinked, but not ionically crosslinked.

As utilized herein, the term "microcapsule" includes capsules of biocompatible gellable material directly surrounding biologically active material. Although the actual dimensions of the invention microcapsules are not critical, the term "microcapsules" includes capsules of biocompatible gellable material the largest dimensions of which typically falls in the range of about 1 $\mu$m up to about 1000 $\mu$m, with a preferable largest dimension falling in the range of about 100 $\mu$m up to about 800 $\mu$m. Commonly, all dimensions of the microcapsule exceed 20 nm. Invention microcapsules can be produced in a variety of shapes, i.e., in the shape of a cylinder (i.e., a geometrical solid generated by the revolution of a rectangle about one of its sides), a sphere (i.e., a solid geometrical figure generated by the revolution of a semicircle around its diameter), a disc (i.e., a generally flat, circular form), a flat sheet (i.e., a generally flat polygonal form, preferably square or rectangular), a wafer (i.e., an irregular flat sheet), a dog-bone (i.e., a shape that has a central stem and two ends which are larger in diameter than the central stem, such as a dumbbell), or the like. Invention microcapsules are generally formed so that the pore size of at least the outer layer of the microcapsule is sufficiently large to allow unhindered diffusion of:

the biologically active material contained therein, or the compound secreted by the biologically active material contained therein, or the compound to be catalyzed and/or reacted by the biologically active material contained therein.

Invention microcapsules are generally formed so that the pore size of at leat the outer layer of the microcapsule is sufficiently small to block inward diffusion of molecules which are capable of initiating an immune response to the biologically active material (e.g., IgG, complement proteins, and the like), at least when the microcapsule is formed to not be contained within a larger macrocapsule.

Biologically active materials contemplated for containment and/or delivery in accordance with the present invention include individual living cells or groups of living cells (e.g., cell aggregates), biological materials (for diagnostic purposes, e.g., for in vivo evaluation of the effects of such biological materials on an organism, and conversely, the effects of the organism on such biological materials), pharmacologically active drugs, diagnostic agents, agents of nutritional value, hemoglobin (to create artificial blood), and the like.

As utilized herein, the term "living cells" includes any viable cellular material, regardless of the source thereof. Thus, virus cells, prokaryotic cells, eukaryotic cells, plant cells, and the like, are contemplated. Specifically contemplated living cells include islets of Langerhans (for the treatment of diabetes) (including individual pancreatic islet cells (e.g., $\alpha$, $\beta$, and $\delta$ cells of pancreatic islets), tumor cells (for evaluation of chemotherapeutic agents), human T-lymphoblastoid cells sensitive to the cytopathic effects of HIV, dopamine secreting cells (for the treatment of Parkinson's disease), nerve growth factor cells (for the treatment of Alzheimer's disease), hepatocytes (for treatment of liver dysfunction), adrenalin/angiotensin secreting cells (for regulation of hypo/hypertension), parathyroid cells (for replacing thyroid function), norepinephrine/metencephalin secreting cells (for the control of pain), and the like. These living cells can be individual cells, or aggregates of cells held together via intercellular adhesion mechanisms characteristic of the individual cells (e.g., islets, and the like).

Examples of pharmacologically active agents include:

analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like), anesthetics (e.g., cyclopropane, enflurane, halothane, isoflurane, methoxyflurane, nitrous oxide, propofol, and the like), antiasthmatics (e.g., Azelastine, Ketotifen, Traxanox, and the like), antibiotics (e.g., neomycin, streptomycin, chloramphenicol, cephalosporin, ampicillin, penicillin, tetracycline, and the like), antidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like), antidiabetics (e.g., biguanides, hormones, sulfonylurea derivatives, and the like), antifungal agents (e.g., griseofulvin, keloconazole, amphotericin B, Nystatin, candicidin, and the like), antihypertensive agents (e.g., propanolol, propafenone, oxyprenolol, Nifedipine, reserpine, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, and the like), anti-inflammatories (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like), antineoplastics (e.g., adriamycin, cyclophosphamide, actinomycin, bleomycin, duanorubicin, doxorubicin, epirubicin, mitomycin, methotrexate, fluorouracil, carboplatin, carnustine (BCNU), methyl-CCNU, cisplatin, etoposide, interferons, camptothecin and derivatives thereof, phenesterine, paclitaxel and derivatives thereof, taxotere and derivatives thereof, vinblastine, vincristine, tamoxifen, etoposide, piposulfan, and the like), antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like), immunosuppressive agents (e.g., cyclosporine, azathioprine, mizoribine, FK506 (tacrolimus), and the like), antimigraine agents (e.g., ergotamine tartrate, propanolol hydrochloride, isometheptene mucate, dichloralphenazone, and the like), sedatives/hypnotics (e.g., barbiturates (e.g., pentobarbital, pentobarbital sodium, secobarbital sodium, and the like), benzodiazapines (e.g., flurazepam hydrochloride, triazolam, tomazeparm, midazolam hydrochloride, and the like), and the like), antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like), and the like), antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like), antimanic agents (e.g., lithium carbonate and the like), antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like), antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like), antigout agents (e.g., colchicine, allopurinol, and the like), anticoagulants (e.g., heparin, heparin sodium, warfarin sodium, and the like), thrombolytic agents (e.g., urokinase, streptokinase, altoplase, and the like), antifibrinolytic agents (e.g., aminocaproic acid and the like), hemorheologic agents (e.g., pentoxifylline and the like), antiplatelet agents (e.g., aspirin, empirin, ascriptin, and the like), anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like), antiparkinson agents (e.g., ethosuximide, and the like), antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorphenirarnine maleate, methdilazine hydrochloride, trimprazine tartrate and the like), agents useful for calcium regulation (e.g., calcitonin, parathyroid hormone, and the like), antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like), antiviral agents (e.g., interferon gamma, zidovudine, amantadine hydrochloride, ribavirin, acyclovir, and the like), antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like), anti-infectives (e.g., GM-CSF and the like), bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium brornide, budesonide, ketotifen, salmeterol, xinafoate, terbutaline sulfate, triamcinolone, theophylline, nedocromil sodium, metaproterenol sulfate, albuterol, flunisolide, and the like), hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium and the like), and the like, hypoglycemic agents (e.g., human insulin, purified beef insulin, purified pork insulin, glyburide, chlorpropamide, glipizide, tolbutamide, tolazamide, and the like), hypolipidemic agents (e.g., clofibrate, dextrothyroxine sodium, probucol, lovastatin, niacin, and the like), proteins (e.g., DNase, alginase, superoxide dismutase, lipase, and the like), nucleic acids (e.g., sense or anti-sense nucleic acids encoding any therapeutically useful protein, including any of the proteins described herein, and the like), agents useful for erythropoiesis stimulation (e.g., erythropoietin and the like), antiulcer/antireflux agents (e.g., famotidine, cimetidine, ranitidine hydrochloride, and the like), antinauseants/antiemetics (e.g., meclizine hydrochloride, nabilone, prochlorperazine, dimenhydrinate, promethazine hydrochloride, thiethylperazine, scopolamine, and the like), oil-soluble vitamins (e.g., vitamins A, D, E, K, and the like), as well as other drugs such as mitotane, visadine, halonitrosoureas, anthrocyclines, ellipticine, and the like, and the like.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, and the like), as well as other diagnostic agents which cannot readily be delivered without some physical and/or chemical modification to accommodate the substantially water insoluble nature thereof.

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

As utilized herein, the term "ionically crosslinkable" means the ability of a biocompatible gellable material to form ionically crosslinked networks in the presence of multivalent cation(s) such as calcium, zinc, barium, strontium, aluminum, iron, manganese, nickel, cobalt, copper, cadmium, lead, and the like, or mixtures of any two or more thereof. This ability is due to the interaction of anions of the biocompatible gellable material (e.g., carboxy groups on alginate) to ionically bond with the multivalent cations. Preferred multivalent cations include calcium, barium, and strontium, with calcium being presently preferred for ionically crosslinking a biocompatible gellable material comprising alginate.

The characterization of an ionically crosslinkable biocompatible gellable material (or any portion thereof) as being "not ionically crosslinked" indicates that an insufficient amount of multivalent cation(s) required to substantially crosslink the biocompatible gellable material is present in the biocompatible gellable material, either because an insufficient amount was always present or because an amount of such multivalent cation(s) was removed by subjecting the biocompatible gellable material to conditions sufficient to substantially disrupt ionic crosslinking in the biocompatible gellable material.

Biocompatible gellable materials contemplated for use in the practice of the present invention include ionically crosslinkable materials, covalently crosslinkable materials, polyionically crosslinkable materials, and the like, and mixtures of any two or more thereof.

Ionically crosslinkable materials contemplated for use in the practice of the present invention include anionic materials which are ionically crosslinkable (e.g., alginates and other polysaccharides, chitosan, gellan gum, xanthan gum, hyaluronic acid, heparin, pectin, carrageenan, and the like), covalently crosslinkable derivatives thereof, and the like, and mixtures of any two or more thereof. Alginates contemplated for use in the present invention include high G-content alginate, high-M content alginate, sodium alginate, and the like, and mixtures of any two or more thereof.

Capsule properties like mechanical strength, pore size, and biocompatibility can be varied with the type and concentration of the alginate employed. For example, alginates with differing $\alpha$-L-guluronic acid (G blocks) to $\beta$-D-mannuronic acid (M blocks) ratios are capable of yielding capsules with significantly differing properties. G blocks have a higher multivalent cation binding capacity than M blocks. In addition, alginates having higher fractions of G blocks are more biocompatible than those containing a larger fraction of M blocks since high M block alginates have been found to induce fibrotic overgrowth. Accordingly, capsules synthesized from alginates with high G/M ratios are generally stronger and more biocompatible than those capsules synthesized from alginates with lower G/M ratios. Thus, the use in accordance with the present invention of alginates having at least 60% or greater G blocks is preferred, with alginates having at least 70% or greater G blocks being presently preferred.

As a further example, alginates with differing molecular weights (MW) or alginate concentrations are capable of yielding capsules with significantly differing properties relating to mechanical strength, pore size, and biocompatibility of the capsule. Thus, it is possible to further modify the end properties of the capsule by choosing alginates of specific types.

Polyionically crosslinkable materials contemplated for use in the practice of the present invention include mixtures of ionically crosslinkable materials and polycationic materials and the like. Polycationic materials contemplated for use in the present invention include polyamino acids (e.g., polyhistidine, polylysine, polyornithine, and the like), polymers containing primary amine groups, secondary amine groups, tertiary amine groups, or pyridinyl nitrogen(s) (such as polyethyleneimine, polyallylamine, polyetheramine, polyvinylpyridine, and the like), covalently crosslinkable derivatives thereof, and the like. Polycationic material molecular weight can vary, depending on the degree of permeability desired. Polycationic material molecular weights will typically fall within a range of about 1,000 to about 100,000 or higher, with a presently preferred molecular weight in the range of about 10,000 up to about 50,000. Presently, preferred polycationic materials for use in the practice of the present invention include polylysine (i.e., poly-D-lysine (PDL), poly-DL-lysine, poly-L-lysine (PLL), poly-$\epsilon$-CBZ-D-lysine, poly-$\epsilon$-CBZ-DL-lysine, poly-$\epsilon$-CBZ-L-lysine), polyornithine (i.e., poly-DL-ornithine, poly-L-ornithine, or poly-$\delta$-CBZ-DL-ornithine), and the like, and mixtures of any two or more thereof.

Covalently crosslinkable materials contemplated for use in the practice of the present invention include covalently crosslinkable polysaccharides (e.g., covalently crosslinkable alginates), covalently crosslinkable polyethylene glycols (i.e., covalently crosslinkable PEGs), covalently crosslinkable polycationic materials, covalently crosslinkable proteins, covalently crosslinkable peptides, other covalently crosslinkable synthetic polymers, and the like, and mixtures of any two or more thereof.

Covalently crosslinkable alginates contemplated for use in the practice of the present invention include alginates modified with a substituent X which is capable of undergoing free radical polymerization (X is a moiety containing a carbon-carbon double bond or triple bond capable of free radical polymerization; and X is linked covalently to the alginate through linkages selected from ester, ether, thioether, disulfide, amide, imide, secondary amines, tertiary amines, direct carbon-carbon (C—C) linkages, sulfate esters, sulfonate esters, phosphate esters, urethanes, carbonates, and the like). Examples of covalently crosslinkable alginates include allyl and vinyl ethers of alginate, acrylate and methacrylate esters of alginate, and the like.

Covalently crosslinkable PEGs contemplated for use in the practice of the present invention include linear or branched chain PEGs (including STAR PEGs) modified with a substituent X which is capable of undergoing free radical polymerization (as described above); wherein X is linked covalently to the PEG through linkages selected from ester, ether, thioether, disulfide, amide, imide, secondary amines, tertiary amines, direct carbon-carbon (C—C) linkages, sulfate esters, sulfonate esters, phosphate esters, urethanes, carbonates, and the like. Examples of such covalently crosslinkable PEGs include vinyl and allyl ethers of PEG; acrylate, diacrylate and methacrylate esters of PEG; and the like; and mixtures of any two or more thereof.

PEGs having a wide range of molecular weights can be employed in the practice of the present invention. Thus, mixtures of different molecular weights for covalently crosslinkable PEGs contemplated for use in the practice of the present invention include PEGs having a MW in the range of about 200 up to about 1,000,000 (with PEGs having molecular weights in the range of about 500 up to about 100,000 being preferred, and PEGs having molecular weights in the range of about 1000 up to about 50,000 being presently preferred). Such PEGs can be linear or branched chain (including STAR PEGs). STAR PEGs are molecules having a central core (such as divinyl benzene) which is anionically polymerizable under controlled conditions to form living nuclei having a predetermined number of active sites. Ethylene oxide is added to the living nuclei and polymerized to produce a known number of PEG "arms," which are quenched with water when the desired molecular weight is achieved. Alternatively, the central core can be an ethoxylated oligomeric glycerol that is used to initiate polymerization of ethylene oxide to produce a STAR PEG of desired molecular weight.

Covalently crosslinkable polycationic materials contemplated for use in the practice of the present invention include polycationic materials modified with a substituent X which is capable of undergoing free radical polymerization (as described above); wherein X is linked covalently to the polycationic material through linkages selected from ester, ether, thioether, disulfide, amide, imide, secondary amines, tertiary amines, direct carbon-carbon (C—C) linkages, sulfate esters, sulfonate esters, phosphate esters, urethanes, carbonates, and the like. Examples of covalently crosslinkable polycationic materials include allyl and vinyl ethers of polycations, acrylate and methacrylate esters of polycations, and the like.

Free radical polymerization of the above-described covalently crosslinkable materials can be carried out in a variety of ways, for example, initiated by irradiation with suitable wavelength electromagnetic radiation (e.g., visible or ultraviolet radiation) in the presence of a suitable photoinitiator, and optionally, cocatalyst and/or comonomer. Alternatively, free radical polymerization can be initiated by thermal initiation by a suitable free radical catalyst.

A variety of free radical initiators, as readily recognized by those of skill in the art, can be employed in the practice of the present invention. Thus, photoinitiators, thermal initiators, and the like can be employed. For example, suitable UV initiators include 2,2-dimethoxy-2-phenyl acetophenone and its water soluble derivatives, benzoin ethyl ether, 2,2-dimethyl phenoxyacetophenone, benzophenone and its water soluble derivatives, benzil and its water soluble derivatives, thioxanthone and its water soluble derivatives, and the like. For visible light polymerization, a system of dye (also known as initiator or photosensitizer) and cocatalyst (also known as cosynergist, activator, initiating intermediate, quenching partner, or free radical generator) are used. Examples of suitable dyes are ethyl eosin, eosin, eosin Y, erythrosin, riboflavin, fluorscein, rose bengal, methylene blue, thionine, and the like; examples of suitable cocatalysts are triethanolamine, arginine, methyl diethanolamine, tiethylamine, and the like.

A small amount of a comonomer can optionally be added to the crosslinking reaction to increase the polymerization rates. Examples of suitable comonomers include vinyl pyrrolidinone, acrylamide, methacrylamide, acrylic acid, ethacrylic acid, sodium acrylate, sodium methacrylate, hydroxyethyl acrylate, hydroxyethyl methacrylate (HEMA), ethylene glycol diacrylate, ethylene glycol dimethacrylate, pentaerythritol triacrylate, pentaerythritol trimethacrylate, trimethylol propane triacrylate, trimethylol propane trimethacrylate, tripropylene glycol diacrylate, tripropylene glycol dimethacrylate, glyceryl acrylate, glyceryl methacrylate, and the like.

Photoinitiators, cocatalysts, and comonomers are collectively referred to as photocomponents, and comprise the active components of the photopolymerizing solution.

Varying the concentrations and proportions of these components in the photopolymerizing solution can be used to yield capsules with different mechanical strengths and differing permeabilities. These factors influence the in vivo shelf life and performance of the capsule after transplantation into the body. In accordance with the present invention, varying the type and amount of the components in the photopolymerizing solution provides a means of controlling capsule properties like mechanical strength, porosity or permeability, and biocompatibility.

Thus, increasing the contact time of the capsule with the photopolymerizing solution gives more time for the photocomponents to diffuse inwards into the capsule. Such enhanced penetration distance, upon photopolymerization, results in a capsule with a greater extent of covalent bonding therethrough. Hence, contact times of the capsule with the photopolymerizing solution determine the depth of photopolymerization relative to the size of the capsule. A capsule that has been uniformly photopolymerized throughout its volume would be expected to result in a homogeneous alginate matrix held together coherently by a uniformly distributed network of covalent bonds, in the absence of interspersed ionic bonds. Such a situation arises when the contact time is sufficiently long that photocomponents are allowed to diffuse throughout the entire volume of the capsule. On the other hand, a capsule that has been photopolymerized only on the surface would be expected to result in a composite capsule with a liquified (e.g., substantially noncrosslinked) core surrounded by a photocrosslinked modified-alginate gel layer on the surface, in the absence of interspersed ionic bonds. Such a situation arises when the contact time is so short that the photocomponents do not diffuse throughout the entire volume of the capsule, but are instead localized in a layer close to the outer surface of the capsule. Upon photopolymerization, the capsule therefore possesses an ionically crosslinked alginate core surrounded by a skin of covalently crosslinked and ionically crosslinked alginate. Subsequent disruption of ionic crosslinking via invention methods yields a composite capsule with a liquified core surrounded by a covalently crosslinked layer.

Capsules (e.g., microcapsules and macrocapsules) contemplated for use in the practice of the present invention may be further characterized as comprising an outer layer and a core. Typically, the outer layer of a capsule comprises that portion of the biocompatible gellable material which is on the outer surface of the capsule, while the core of a capsule is that portion of the biocompatible gellable material which is not the outer layer.

Generally, the outer layer of a capsule has a thickness of at least about $\frac{1}{500}^{th}$ of the largest dimension of the capsule (e.g., 1 micron for 500 micron macrocapsule), with a thickness of at least about $\frac{1}{25}^{th}$ to about $\frac{2}{25}^{th}$ of the largest dimension of the capsule (e.g., 20–40 microns for 500 micron macrocapsule) being preferred, and a thickness of at least about $\frac{1}{10}^{th}$ of the largest dimension of the capsule (e.g., 50 microns for 500 micron macrocapsule) being presently preferred. When the outer layer of a capsule has been covalently crosslinked and optionally polyionically crosslinked, this enhanced thickness of the outer layer provides enhanced immunogenic protection (e.g., enhanced prevention of direct exposure of any immunogenic agents at the capsule surface (e.g., polycations, unencapsulated biologically active materials, and the like)) and enhanced stability (e.g., stability to long-term exposure to physiological conditions), when compared to prior art microcapsules.

The core of a capsule contemplated for use in the practice of the present invention can optionally be covalently crosslinked and/or ionically crosslinked. Thus, in one aspect, invention microcapsules can comprise a biocompatible gellable material whose core is ionically crosslinked. In a further aspect, invention microcapsules can comprise a biocompatible gellable material whose core is both covalently crosslinked and ionically crosslinked. In an additional aspect, invention microcapsules can comprise a biocompatible gellable material whose core is covalently crosslinked, but not ionically crosslinked. In another aspect, invention microcapsules can comprise a biocompatible gellable material whose core is neither ionically crosslinked nor covalently crosslinked.

In accordance with the present invention, there are further provided macrocapsules containing biologically active materials therein, optionally contained in at least one microcapsule therein. Invention macrocapsules comprise a first biocompatible gellable material which is ionically crosslinkable and which contains the biologically active materials (and optionally present microcapsules) therein. When the microcapsules are not present within the macrocapsule, invention macrocapsules are further characterized in that at least the outer layer of the macrocapsule is covalently crosslinked and optionally polyionically crosslinked, but not ionically crosslinked. When the microcapsules are present within the macrocapsule, invention macrocapsules are further characterized in that at least the outer layer of the macrocapsule is covalently crosslinked, polyionically crosslinked, or both covalently crosslinked and polyionically crosslinked, but not ionically crosslinked, and each of the microcapsules contained within invention macrocapsules comprises a second biocompatible gellable material containing the biologically active materials therein.

As utilized herein, "macrocapsule" includes capsules of gel material surrounding biologically active material, optionally contained within at least one microcapsule. The term "macrocapsule" can include "macro-membranes," "macrogels," "gel entrapped microcapsules," "lace," "noodles," "teabags," "threads," "worms," and the like. Although the actual dimensions of the invention macrocapsules are not critical, the term "macrocapsules" includes capsules of biocompatible gellable material the largest dimensions of which typically fall in the range of about 1000 μm up to about 50000 μm. Commonly, all dimensions of the invention macrocapsules are greater than 20 nm. Invention macrocapsules can be produced in a variety of shapes, i.e., in the shape of a cylinder (i.e., a geometrical solid generated by the revolution of a rectangle about one of its sides), a sphere (i.e., a solid geometrical figure generated by the revolution of a semicircle around its diameter), a disc (i.e., a generally flat, circular form), a flat sheet (i.e., a generally flat polygonal form, preferably square or rectangular), a wafer (i.e., an irregular flat sheet), a dog-bone (i.e., a shape that has a central stem and two ends which are larger in diameter than the central stem, such as a dumbbell), or the like. The macrocapsule is generally formed so that the pore size of at least the outer layer of the macrocapsule is sufficiently large to allow unhindered diffusion of:

the biologically active material contained therein, or the biologically active compound (e.g., insulin) secreted by the biologically active material (e.g., pancreatic islet cells) contained therein, or the compound to be catalyzed and/or reacted by the biologically active material contained therein, while being sufficiently small to block inward diffusion of molecules which are capable of initiating an immune response to the biologically active material (e.g., IgG, complement proteins, and the like).

Like the core of the invention microcapsules, the core of the invention macrocapsules can typically be covalently crosslinked and/or ionically crosslinked. Thus, in one aspect, invention macrocapsules comprise a core that is ionically crosslinked. In a further aspect, invention macrocapsules comprise a core that is both covalently crosslinked and ionically crosslinked. In an additional aspect, invention macrocapsules can comprise a core that is covalently crosslinked, but not ionically crosslinked. In another aspect, invention microcapsules can comprise a core that is neither ionically crosslinked nor covalently crosslinked.

Similar to the outer layer of the invention microcapsules, the outer layer of the optional microcapsule(s) contemplated for use as part of the invention macrocapsules commonly is ionically crosslinked, covalently crosslinked, polyionically crosslinked, or any suitable combination of any two or more thereof. Thus, in one aspect, invention macrocapsules can comprise at least one microcapsule, wherein at least the outer layer of the microcapsule(s) is covalently crosslinked. In an additional aspect, invention macrocapsules can comprise at least one microcapsule, wherein the outer layer of the microcapsule(s) is polyionically crosslinked. In another aspect, invention macrocapsules can comprise at least one microcapsule, wherein at least the outer layer of the microcapsule(s) is ionically crosslinked.

Typically, the core of the optional microcapsule(s) contemplated for use as part of the invention macrocapsules is covalently crosslinked and/or ionically crosslinked. Thus, in one aspect, the core of the microcapsule(s) contemplated for use as part of the invention macrocapsules is ionically crosslinked. In a further aspect, the core of the microcapsule(s) contemplated for use as part of the invention macrocapsules is covalently crosslinked and ionically crosslinked. In another aspect, the core of the microcapsule(s) contemplated for use as part of the invention macrocapsules is covalently crosslinked, but not ionically crosslinked. In an additional aspect, the core of the microcapsule(s) contemplated for use as part of the invention macrocapsules is neither ionically crosslinked nor covalently crosslinked.

Capsules (e.g., microcapsules and macrocapsules) can be manufactured by various techniques known to those of skill in the art, including but not limited to interfacial polycondensation, emulsion polymerization, simple and complex coacervation, thermal and ionic gelation, phase separation, electrostatic precipitation, solvent evaporation, and mechanical agitation. The specific manufacturing technique employed is dictated by various factors, including the chemistry of the biocompatible gellable material (i.e., the capsule shell material), the properties desired of the capsule manufactured thereby, and the like.

Biocompatible gellable material (e.g., alginate)—containing microcapsules (and biocompatible gellable material—containing macrocapsules which comprise microcapsules) are generally produced employing a co-axial pneumatic nozzle. The biocompatible gellable material solution (which contains the encapsulant (e.g., the biologically active material (for microcapsules and/or macrocapsules), or the microcapsules containing the biologically active material (for macrocapsules)) is extruded through the central bore, with air flowing around the solution. The air pressure provides the force necessary to break up the extruded biocompatible gellable material solution into droplets. In such a system, the droplet size can be altered by varying the ratio of the solution flow rate to the air flow rate. Increasing the latter relative to the former yields smaller droplets.

Macrocapsules can also be synthesized by extruding the biocompatible gellable material solution manually through a syringe attached with a needle. The droplets detach from the needle when the drop size becomes big enough that the gravitational force tending to dislodge the droplet from the needle exceeds the forces of surface tension tending to keep the droplet attached to the needle. The size of the droplets can be controlled by choosing needles with an appropriate gauge.

Once the droplets of biocompatible gellable material solution have been formed, they can be subjected to a variety of crosslinking conditions.

In one variety of crosslinking conditions, the droplets of biocompatible gellable material solution are ionically crosslinked and covalently crosslinked to form capsules, and then subjected to conditions sufficient to disrupt ionic crosslinking in at least the outer layer of the capsule. Under this aspect, the droplets are first subjected to conditions sufficient to ionically crosslink the ionically crosslinkable material solution. Typically, these conditions comprise contacting the droplets with an ionic crosslinking medium containing at least one multivalent cation(s) (e.g., calcium) to yield ionically crosslinked capsules (e.g., ionically crosslinked microcapsules and ionically crosslinked macrocapsules). These ionically crosslinked capsules are subsequently (or, optionally, simultaneously) contacted with the photopolymerizing solution for a predetermined amount of time. During this time, the components of the photopolymerizing solution (that is, photoinitiators, cocatalysts, and/or comonomers) diffuse inwards into the ionically crosslinked capsule.

As readily recognized by those of skill in the art, the predetermined time can be varied as a function of the size of the capsule (i.e., smaller capsules have larger ratios of surface area to volume, and thus require less time for equivalent diffusion of photocomponents), the concentration of the individual components in the photopolymerizing solution and their concentrations relative to each other (i.e., different concentrations yield different properties of capsule), and the like. In addition, the predetermined time can be altered in order to vary the extent of the covalent crosslinkability relative to the ionic crosslinkability of the capsule.

The ionically crosslinked capsule containing the photocomponents can then optionally be subsequently transferred to another solution containing a concentration of the multivalent cation(s) (e.g., $Ca^{2+}$) which is sufficiently high to maintain an intact ionically crosslinked droplet, yet sufficiently low (and definitely lower than the concentration of the ionically crosslink initiating first multivalent cation(s) solution) to prevent mineralization due to possible local supersaturation of the multivalent cation (e.g., $Ca^{2+}$) within the droplet.

The ionically crosslinked capsules are then subsequently (or, optionally, simultaneously) subjected to covalent crosslinking conditions (e.g., photopolymerization (such as under visible light from high pressure 100 W mercury lamps (strong emission at wavelength of about 500 nm to about 550 nm) or argon ion laser light (wavelength of 514 nm at powers between about 10 mW to about 2 W))). The covalent crosslinking time is generally rapid (on the order of milliseconds (for photopolymerization via an argon ion laser) to seconds (for photopolymerization via a mercury lamp)), and varies with the concentrations of biocompatible gellable material, initiator, cocatalyst, and comonomers in the ionically crosslinked capsule.

The time interval between the ionic crosslinking and the covalent crosslinking of the droplets can be varied. This time interval can vary from 0 seconds (e.g., simultaneously subjecting the droplets to ionic crosslinking conditions and covalent crosslinking conditions) to about 5 minutes. The shorter the time interval, the smaller the possibility exists that the photocomponents will diffuse out of the droplets and weaken the covalent crosslinking process, and the greater the probability that a stable covalently crosslinked capsule will be formed. This is especially applicable to smaller sized droplets (e.g., microcapsules or smaller macrocapsules), as their larger ratios of surface area (e.g., diffusion surface) to volume increase the potential for loss of photocomponents, and decrease the probability that a stable covalently crosslinked capsule will be formed.

Subsequent to ionic crosslinking and covalent crosslinking, the capsules can optionally be rinsed thoroughly with saline in order to remove excess multivalent cation(s) (whose removal helps reduce the chance of biomineralization) and unreacted photocomponents (whose removal helps reduce potential toxicity effects of these photocomponents on the biologically active materials). The capsules can optionally be incubated at about 37° C. in a suitable culture medium.

Additional alternative treatments that can follow the covalent crosslinking step include subjecting the capsule to conditions sufficient to disrupt ionic crosslinking in at least the outer layer of the capsule. This disruption of ionic crosslinking can promote migration and aggregation of the biologically active material, as well as transport of the biologically active material or components secreted by the biologically active material out of the capsule.

Thus, in accordance with the present invention, there are additionally provided methods of making a microcapsule having substantially no ionic crosslinking in at least the outer layer thereof and containing biologically active materials therein. Invention methods for making such microcapsules comprise:

subjecting a microcapsule, wherein at least the outer layer thereof is ionically crosslinked, and wherein at least the outer layer thereof is covalently crosslinked and optionally polyionically crosslinked, and which contains biologically active materials therein, to conditions sufficient to disrupt ionic crosslinking in at least the outer layer thereof, thereby forming a microcapsule having substantially no ionic crosslinking in at least the outer layer thereof.

In accordance with the present invention, there are further provided methods of making a macrocapsule having substantially no ionic crosslinking in at least the outer layer thereof and containing biologically active materials therein, optionally contained within at least one microcapsule. Invention methods for making such macrocapsules comprise:

subjecting a macrocapsule, wherein at least the outer layer thereof is ionically crosslinked, and which contains biologically active materials therein, to conditions sufficient to disrupt ionic crosslinking in at least the outer layer thereof, thereby forming a macrocapsule having substantially no ionic crosslinking in at least the outer layer thereof. When microcapsules are not present within the macrocapsule, the macrocapsule can be further characterized in that at least the outer layer thereof is covalently crosslinked and optionally polyionically crosslinked. When microcapsules are present within the macrocapsule, the macrocapsule can be further characterized in that at least the outer layer thereof is covalently crosslinked, polyionically crosslinked, or both covalently crosslinked and polyionically crosslinked.

Conditions sufficient to disrupt ionic crosslinking, either in at least the outer layer or the core of a microcapsule, a macrocapsule or their constituent biocompatible gellable materials, include contacting the relevant microcapsule, macrocapsule or their constituent biocompatible gellable materials with a solution of sodium citrate, ethylenediaminetetraacetic acid (EDTA), diethylenetriaminepentaacetic acid (DTPA), and other biocompatible chelators of multivalent cations, and the like, and mixtures of any two or more thereof, in a concentration sufficient to chelate sufficient cations to substantially disrupt ionic crosslinking in the relevant microcapsule, macrocapsule or their constituent biocompatible gellable materials. In a preferred embodiment, conditions sufficient to disrupt ionic crosslinking in at least the outer layer of a capsule or constituent biocompatible gellable material comprise contacting the capsule or constituent biocompatible gellable material with a solution of sodium citrate having a concentration in the range of about 15 mM to about 1M.

In an alternative embodiment of the invention, capsules which are covalently crosslinked but not ionically crosslinked, are prepared by directly covalently crosslinking, without first ionically crosslinking, the droplets of biocompatible gellable solution formed as described above.

Thus, in accordance with this aspect of the present invention, there are provided alternative methods of making a microcapsule containing biologically active materials therein, wherein droplets comprising a suspension of biologically active materials in a covalently crosslinkable carrier are simultaneously subjected to:

conditions sufficient to prevent substantial dissociation thereof, and conditions sufficient to induce substantial covalent crosslinking thereof, thereby forming the microcapsule. Invention methods of making microcapsules are optionally characterized, in one aspect, in that no ionic crosslinking is required (although such ionic crosslinking may be present) to stabilize the droplet prior to covalent crosslinking thereof, as the conditions sufficient to prevent substantial dissociation of the droplet perform the requisite stabilizing function of ionic crosslinking.

As utilized herein, the term "covalently crosslinkable carrier" includes all covalently crosslinkable materials as described herein.

Conditions sufficient to prevent substantial dissociation of the droplet include contacting the droplet with a medium which is substantially immiscible with the droplet and which does not substantially inhibit the induction of covalent crosslinking. Media which are substantially immiscible with the droplet include those media which are capable of solvating less than 10% of the volume of the droplet during the time period in which the droplet is in contact with the media. Media which do not substantially inhibit the induction of covalent crosslinking include media which conduct sufficient electromagnetic energy from an energy source to the droplet to enable initiation of covalent crosslinking in the covalently crosslinkable carrier, without destroying the functionality of the biologically active material.

Media which are substantially immiscible with the droplet and which do not substantially inhibit the induction of substantial covalent crosslinking also comprise, for aqueous droplets comprising biocompatible gellable materials contemplated for use in accordance with the present invention, soybean oil, coconut oil, safflower oil, sunflower oil, sesame oil, other vegetable oils, and the like. In a preferred embodiment, such a solution comprises soybean oil.

Conditions sufficient to induce substantial covalent crosslinking of the droplet include irradiating the droplet with sufficient energy to induce photocrosslinking of the covalently crosslinkable carrier. This energy is generally in the form of electromagnetic radiation, such as visible light, ultraviolet (UV) radiation, or lasers, although this energy can also include thermal energy. Two preferred embodiments of such conditions include contacting the droplet with an argon ion laser at a wavelength of about 514 nm and at a power level in the range of about 10 mW to about 2 W for no more than about 50 milliseconds, and contacting the droplet with a high pressure (e.g., about 100 W) mercury lamp for no more than about 5 minutes.

In accordance with another aspect of the present invention, there are provided alternative methods of making a macrocapsule containing biologically active materials therein, wherein droplets, comprising a suspension of the biologically active materials, optionally contained within at least one microcapsule, in a covalently crosslinkable carrier, are simultaneously subjected to:

conditions sufficient to prevent substantial dissociation thereof, and conditions sufficient to induce substantial covalent crosslinking thereof, thereby forming the macrocapsule. Invention methods of making macrocapsules are optionally characterized, in one aspect, in that no ionic crosslinking is required (although such ionic crosslinking may be present) to stabilize the droplet prior to covalent crosslinking thereof, as the conditions sufficient to prevent substantial dissociation of the droplet perform the requisite stabilizing function of ionic crosslinking.

Capsules which comprise individual cells capable of forming cell aggregates and which have been formed in accordance with the foregoing invention methods can be further characterized in that they are capable of facilitating migration of the cells within the core of the capsules, and aggregation of the cells to form cell aggregates.

Thus, in accordance with the present invention, there are additionally provided capsules (e.g., microcapsules and macrocapsules) containing at least one cell aggregate therein. Invention capsules comprise an ionically crosslinkable biocompatible gellable material, and have a core and an outer layer, wherein at least the outer layer of the capsule is covalently crosslinked or polyionically crosslinked or both covalently crosslinked and polyionically crosslinked, but not ionically crosslinked, and wherein said at least one cell aggregate is contained within the core which is not ionically crosslinked.

When the capsule is a macrocapsule containing microcapsules, there are at least two possible embodiments of this aspect of the invention. In a first embodiment, at least the core of the microcapsule(s) of the macrocapsule is not ionically crosslinked, and the cell aggregate(s) is formed and contained within the core of the microcapsule(s) of the macrocapsule. In a second embodiment, at least the core of the macrocapsule is not ionically crosslinked, and the cell aggregate(s) is formed and contained within the core of the macrocapsule.

As utilized herein, "cell aggregate" includes an aggregation of individual living cells. Presently preferred cell aggregates include pseudo islets, which are aggregates of individual pancreatic islet cells (including a, β, or δ pancreatic islet cells). The cell aggregates are formed within the microenvironment created by a capsule. Such a microenvironment as is present within the capsule provides a low-stress medium for the aggregation of single cells into clumps of cells, or cell aggregates. The cell aggregates can, under at least some conditions, optionally be further characterized as exhibiting properties and functionality substantially identical to those of naturally occurring islets of corresponding cells in vivo. Accurate control over the average number and size of cell aggregates encapsulated in each capsule can be achieved by controlling the number of cells present per capsule. Thus, the number of cells present per capsule could be varied by:

varying the culturing conditions for the unencapsulated individual cells (i.e., varying the number of cell division cycles experienced by each unencapsulated individual cell), and/or varying the encapsulating conditions for the unencapsulated individual cells (i.e., varying the number of individual cells per microcapsule), and/or varying the culturing conditions for the encapsulated individual cells (i.e., varying the number of cell division cycles experienced by each encapsulated individual cell).

In accordance with the present invention, there are additionally provided methods of making a capsule containing at least one cell aggregate therein. Invention methods comprise subjecting a capsule comprising an ionically crosslinked biocompatible gellable material wherein at least the outer layer of the capsule is covalently crosslinked or polyionically crosslinked or both covalently crosslinked and polyionically crosslinked, wherein said capsule encapsulates a plurality of individual cells, to conditions sufficient to disrupt ionic crosslinking within the core of the capsule.

Invention methods of making a capsule containing at least one cell aggregate therein can be optionally characterized, in one aspect, in that the ionic interactions within the capsule are sufficiently reduced to facilitate migration of the individual cells within the capsule, thereby facilitating aggregation and formation of at least one cell aggregate within the capsule.

When the capsule is a macrocapsule containing microcapsules, there are at least two possible embodiments of this aspect of the invention method. In a first embodiment, at least the core of the microcapsule(s) of the macrocapsule is subjected to conditions sufficient to disrupt ionic crosslinking within the core of the microcapsule(s) of the macrocapsule, thereby rendering the core not ionically crosslinked, and the cell aggregate(s) is formed and contained within the core of the microcapsule(s) of the macrocapsule. In a second embodiment, at least the core of the macrocapsule is subjected to conditions sufficient to disrupt ionic crosslinking within the core of the microcapsule(s) of the macrocapsule, thereby rendering the core not ionically crosslinked, and the cell aggregate(s) is formed and contained within the core of the macrocapsule.

Proliferation of the individual cells within the capsule can be desirable because the number, size and rate of formation of the cell aggregates can be directly proportional to the number of individual cells present within the capsule. Where proliferation of the individual pancreatic islet cells is desired, the invention methods of making a capsule containing at least one cell aggregate therein can optionally further include the step of:

subjecting the capsule to conditions sufficient to promote proliferation of the at least one individual cell.

This step can take place either before or after the step of subjecting the capsule to conditions sufficient to disrupt ionic crosslinking within the core of the capsule, as described above.

Conditions sufficient to promote proliferation of the individual pancreatic cells include contacting the individual pancreatic cells with a suitable culture medium.

In accordance with the present invention, there are also provided delivery systems for biologically active materials. Invention delivery systems comprise the invention microcapsules and/or the invention macrocapsules. The biologically active materials contemplated for use with the invention delivery systems include the biologically active materials contemplated for use with the invention microcapsules and the invention macrocapsules.

All references cited in this application are hereby incorporated herein by reference in their entirety, including the entire contents of U.S. patent application Ser. No. 09/076,339, Filed: May 11, 1998.

The invention will now be described in greater detail with reference to the following non-limiting examples. Those of ordinary skill in the art, when guided by the teachings of the specification, may discover during the term of this patent other embodiments of this invention which fall within the scope of the appended claims.

EXAMPLE 1

Method of Testing Strength of Microcapsules

The effect of varying the concentrations of the components comprising the photopolymerizing solution (i.e., photoinitiators, cocatalysts, and comonomers) both individually and relative to each other has been characterized based on evaluation of bead strength. Trends in bead strengths provide a window into understanding the efficiency of ionic and covalent crosslinking. In general, a higher bead strength indicates a stronger or closely crosslinked matrix. Such a matrix is expected to have a smaller pore size due to the increased density of covalent crosslinking between the polymer molecules. Based on such analysis, evaluating bead strengths provides an insight into mechanical properties, diffusional properties (porosity and permeability), and in vivo end performance of such capsules used for xenotransplantation. Such experiments help construct an experimental database to intelligently manipulate capsule production conditions so as to yield capsules with desired end properties.

Modified alginate (acrylate derivatized alginate or AA) utilized in this Example 1 was prepared by chemically modifying alginate by the incorporation of acrylate groups. The method for modification is included in U.S. Pat. No. 5,700,848, Issue Date: Dec. 23, 1997, the entire contents of which are hereby incorporated by reference herein.

Modified-alginate, ionically crosslinked beads (comprising 2% AA) of 700 $\mu$m average diameter were synthesized by the conventional coaxial pneumatic nozzle technique. Three photopolymerizing solutions were used: 1×eosin (EE)/triethylamine (TEA)/vinyl pyrrolidinone (VP) (each at a concentration of 0.025 g/L, 2.5 ml/L, and 5 ml/L respectively), 2×EE/TEA/VP (each at a concentration of 0.05 g/L, 5 ml/L, and 10 ml/L respectively), and 1×eosin Y (EY)/TEA/VP (each at a concentration of 0.025 g/L, 2.5 ml/L, and 5 ml/L respectively). The time of exposure of the beads to the photopolymerizing solution (also referred to as soaking time) was systematically varied, while the photopolymerization time was kept constant at 5 minutes. The mechanical integrity of the covalently crosslinked beads thereby synthesized was tested by subsequent immersion in 1M sodium citrate, followed by immersion in deionized water. Strength analysis of the beads was performed using Texture Analyzer (Stable Micro Systems, UK). The results are presented in the following table:

| Soaking time, min | Average strength of six microbeads, g | | |
|---|---|---|---|
| | 1 × EE/TEA/VP | 2 × EE/TEA/VP | 1 × EY/TEA/VP |
| 1 | 157.2 | 215.1 | 12.55 |
| 5 | 201.2 | 403.9 | 136.6 |

It is seen from the above table that as the concentrations of the photocomponents are doubled, the bead strength increases significantly, when the rest of the processing conditions are identical. This is because higher concentrations of photocomponents can result in a greater extent of covalent crosslinking contributing to the increased bead strength. For the same photopolymerizing solution, increasing the soaking time of the beads in the photopolymerizing solution results in beads with increased strength upon polymerization. This is because increased soaking time allows longer time for the photocomponents to diffuse in the bead resulting in a greater penetration distance. Subsequent photopolymerization results in a stronger bead due to a greater extent of covalent crosslinking. It is also seen from the above table that under identical experimental conditions and at identical concentrations, EE results in the formation of a stronger bead than EY. This can be attributed to the additional hydrophobic interactions EE is capable of participating in as compared to EY, due to the more hydrophobic nature of EE compared to EY.

Additional experiments were done by systematically varying the concentration of each of the components comprising the photopolymerizing solution, while keeping the concentrations of the rest of the components identical. In a certain range of concentrations it was found that each of the photocomponents contribute to bead strength. That is, in a certain range of concentrations, increasing the concentration of the photoinitiator, cocatalyst, and comonomer either individually or in combination relative to the other components results in beads with increased strengths after photopolymerization.

Thus, varying the concentrations of components in the photopolymerizing solution in addition to varying the soaking time of the beads in such solutions provides a convenient means of controlling capsule properties like mechanical strength, porosity, and consequently in vivo end performance of the capsule after xenotransplantation.

EXAMPLE 2

Method of Forming Macrocapsules Having at Least their Outer Layer not Ionically Crosslinked Modified alginate (acrylate derivatized alginate or AA) utilized in this Example 2 was prepared in accordance with the method described in Example 1.

Freshly harvested human islet cells were encapsulated in AA macrocapsules by extruding a mixture of the AA (at a concentration of 2% in saline) and islet cells through a syringe attached with a 23 G or 21 G needle into a $Ca^{2+}$-rich solution (36 mM $CaCl_2$). The calcium ionically crosslinked the AA matrix, resulting in spherical ionically crosslinked beads approximately 2 mm in diameter. These beads were then immersed in a photopolymerizing solution consisting of eosin Y (0.025 g/l) (EY), triethyl amine (2.5 ml/l) (TEA), and vinyl pyrrolidinone (5 ml/l) (VP). The photocomponents were allowed to diffuse into the macrocapsules for 5 min. The macrocapsules were subsequently transferred to a solution with a lower level of calcium (10 mM $CaCl_2$), and then immediately photopolymerized using 100 W high pressure mercury lamps. The photopolymerization was carried out for 5 min. The resulting covalently crosslinked macrocapsules were washed thoroughly with saline to remove any unbound calcium or unreacted components of the photopolymerizing solution.

The covalently crosslinked, ionically crosslinked macrocapsules were treated by immersion for 5 min in a sodium citrate solution (55 mM). Such treatment yielded a macrocapsule solely crosslinked by covalent linkages without the ionic linkages.

In vitro viability of the encapsulated human islets was examined in this group of capsules by acridine orange/propidium iodide (AO/PI) staining. Function of the encapsulated islets was examined and quantified by static glucose stimulation (SGS). Unencapsulated (or free) islet viability and function was assessed similarly. Briefly, the SGS technique involves stimulation of islets with a high level of glucose and measurement of the secreted insulin (by RIA) in response to the glucose level. During SGS, either encapsulated or unencapsulated islets were incubated in RPMI culture medium containing a basal level of 60 mg % glucose for 60 minutes, then transferred to a medium containing a stimulatory level of 450 mg % glucose for 60 minutes, and returned to basal medium (60 mg % glucose) for a further 60 minutes. The supernatant was collected at the end of each 60 minute period. Insulin secretion was assayed using RIA by measuring insulin concentration ($\mu$U/ml per islet equivalent count) in the supernatant.

An increase in the secreted insulin level above the basal secretion during the stimulation phase, followed by a return in secreted insulin to basal levels is a requisite for good islet function. The viability of the islets in this group of capsules and in the free islets was quite high (70–85%), indicating that the encapsulation environment was not toxic to the cells.

The encapsulated islets were also found to be functional in the group of capsules, yielding a SGS index of 5.14, as compared to an index of 9.59 for free islets. In such tests, an index >3 is indicative of healthy islets. The encapsulated islets compared well to encapsulated islets where there was no treatment with sodium citrate. The SGS index for these untreated, encapsulated islets was 6.01.

These tests show that the encapsulation system employed in this example (i.e., encapsulation followed by treatment with sodium citrate) is non-toxic to the cells, and the encapsulated islets remain healthy and retain normal function in such a microenvironment.

EXAMPLE 3

Method of Making Covalently Crosslinked Capsules not Requiring Prior Ionic Crosslinking Modified alginate (acrylate derivatized alginate or AA) utilized in this Example 3 was prepared in accordance with the method described in Example 1. In addition, modified PEG (PEG diacrylate or PEGDA) was prepared by chemically modifying PEG by the incorporation of acrylate groups. The method for modification is included in U.S. patent application Ser. No. 09/076,339, Filed: May 11, 1998, the entire contents of which are hereby incorporated by reference herein.

Photopolymerized AA and PEGDA coated capsules (e.g., microcapsules and macrocapsules), which directly contained cells or contained cells further encapsulated in alginate microcapsules, were prepared in accordance with this Example 3.

The apparatus for synthesizing these capsules consisted of a system of coaxial nozzles surrounded by an air jacket. The inner nozzle had a 22 G bore, and the outer nozzle had a 16 G bore. The encapsulant (or the biologic to be encapsulated) was to be extruded through the inner nozzle, while the biocompatible gellable material was to be simultaneously extruded through the outer nozzle. Air/nitrogen was to be pumped through the outer jacket. The air flow rate was to be adjusted to yield capsules of differing sizes. For example, increasing the air flow rate relative to the liquid flow rate would result in synthesis of smaller capsules.

A suspension of cells (for microcapsule formation) or a suspension of the alginate microcapsules (for macrocapsule formation) was prepared. The alginate microcapsules with the cells encapsulated in them were produced using the conventional coaxial pneumatic nozzle system.

AA and PEGDA were dissolved in a solution comprising deionized water, the photoinitiator (EY), cocatalyst (TEA), and comonomer (VP). The suspension (i.e., of cells, or of the alginate microcapsules) was extruded through the inner nozzle, while the solution containing AA, PEGDA, and the photocomponents was simultaneously extruded through the outer nozzle. The extruded droplets were allowed to fall into soybean oil. This resulted in a water-in-oil (w/o) emulsion, in which oil prevented the dissociation of the hydrophilic droplets. These droplets in the w/o emulsion were simultaneously exposed to light from high pressure mercury lamps (100 watts). The photocomponents promoted covalent crosslinking of the AA and PEGDA biocompatible gellable material in the presence of the mercury lamp light. This resulted in the formation of a capsule coated by a mixture of biocompatible materials (AA and PEGDA), in which each of the polymers is linked together (and possibly to each other) by covalent crosslinking, and in which the capsule is further characterized by an absence of ionic crosslinking. The core of such a capsule is either the cell suspension or a suspension of alginate microspheres containing the cells.

The capsules can be isolated from the w/o emulsion by filtration through a sieve with a suitable mesh rating, followed by repeated washings of the capsules with water. Alternatively, the capsules can be recovered by the addition of excess water in a separatory funnel, thereby allowing the hydrophilic capsules to migrate to the water phase. This can be done either in the presence or absence of a biocompatible phase transfer agent. Repeated washings should be done to ensure satisfactory removal of the oil phase.

EXAMPLE 4

Preparation of Microcapsules Containing Cell Aggregates therein

Microcapsules, comprising unmodified alginate, a biocompatible gellable material which is ionically crosslinkable, that encapsulates individual cells which are a coculture of $\alpha$, $\beta$, and $\delta$ cells of pancreatic islets, were synthesized by the conventional coaxial pneumatic nozzle technique. These microcapsules were then immersed in a solution of polylysine (PL), thereby resulting in a coating of PL around the alginate capsules to form an outer layer of the biocompatible gellable material which was polyionically crosslinked. The resulting microcapsules were unmodified alginate-polylysine (APL) microcapsules. After coating the microcapsules with PL, the core of these microcapsules was liquified by degelling them through immersion of the microcapsules in sodium citrate (55 mM).

The microcapsules were then left standing. Upon standing, the individual pancreatic islets cells within the microcapsule tended to aggregate in the microcapsule, resulting in the formation of cell aggregates.

This Example 4 demonstrates that cell aggregates can more easily form in a capsule when the core of the capsule is not ionically crosslinked.

EXAMPLE 5

Preparation of Microcapsules for Aggregation of Proliferated Cells

Alginate-PLL microcapsules, ranging from 300–1000 $\mu$m in diameter, were synthesized by pneumatic coaxial extrusion in accordance with the techniques described herein. The average size of the microcapsule in the current application was 800 $\mu$m±70 $\mu$m.

The initial loading of human pancreatic single cells was in the range of $5 \times 10^6$ to $15 \times 10^6$ cells/ml of the alginate solution. In this particular application, the aforementioned cell loading translates to approximately 1300–4000 single cells/microcapsule. Upon aggregation of the cells within the microcapsule after degelling the microcapsule via sodium citrate treatment and after contacting the microcapsule with a suitable culture medium, it was observed that a loading of 1–15 pancreatic cell aggregates/microcapsule was achieved.

The "cell aggregates" formed as described above were morphologically similar to that of native, freshly isolated human islets, suggesting that the microcapsule indeed provided a low-stress environment for cell aggregation. These cell aggregates were both viable and functional as established through viability and function tests.

Cell viability was assessed by acridine orange/propidium iodide (AO/PI) staining, while function was assessed by Static Glucose Stimulation (SGS) tests. The cell aggregates had a viability $\geq 75\%$ (usually, 70–90%), indicating that the cell aggregates generated as described above were healthy islets. SGS indicated a stimulation index (SI) $\geq 2.0$ (usually, $2.0 \leq SI \leq 40$), suggesting that the aforementioned cell aggregates are capable of normal insulin secretion function. Successful reversal of diabetes was achieved in STZ-induced diabetic rats after transplantation of the encapsulated cell aggregates into these rats. These tests indicate that the cell aggregates are healthy and viable, and are capable of both in vitro and in vivo function. Details of the AO/PI stain and SGS test referenced above are described in Example #2 of U.S. patent application Ser. No. 09/076,339, Filed: May 11, 1998, the entire contents of which have already been incorporated herein by reference.

This Example 5 demonstrates that viable, functional cell aggregates can readily form in a capsule.

While the invention has been described in detail with reference to certain preferred embodiments thereof, it will be understood that modifications and variations are within the spirit and scope of that which is described and claimed.

That which is claimed is:

1. A macrocapsule containing biologically active materials therein, wherein:

said macrocapsule comprises a core and an outer layer, wherein:

the core comprises a first biocompatible gellable material which is ionically crosslinkable and which optionally contains at least one microcapsule therein, wherein, when at least one microcapsule is present, each microcapsule comprises a second biocompatible gellable material containing the biologically active materials therein, wherein:

at least the outer layer of said macrocapsule is covalently crosslinked or polyionically crosslinked or both polyionically crosslinked and covalently crosslinked, but not ionically crosslinked, and wherein:

when microcapsules are not present, at least the outer layer of said first biocompatible gellable material is covalently crosslinked and optionally polyionically crosslinked, but not ionically crosslinked.

2. The macrocapsule according to claim 1, wherein the core of said macrocapsule is ionically crosslinked.

3. The macrocapsule according to claim 2, wherein the core of said macrocapsule is covalently crosslinked.

4. The macrocapsule according to claim 1, wherein the core of said macrocapsule is covalently crosslinked.

5. The macrocapsule according to claim 4, wherein the core of said macrocapsule is not ionically crosslinked.

6. The macrocapsule according to claim 1, wherein the core of said macrocapsule is not ionically crosslinked.

7. The macrocapsule according to claim 1, wherein at least the outer layer of each of said microcapsules is covalently crosslinked.

8. The macrocapsule according to claim 7, wherein the core of each of said microcapsules is covalently crosslinked.

9. The macrocapsule according to claim 2, wherein at least the outer layer of each of said microcapsules is covalently crosslinked.

10. The macrocapsule according to claim 9, wherein the core of each of said microcapsules is covalently crosslinked.

11. The macrocapsule according to claim 3, wherein at least the outer layer of each of said microcapsules is covalently crosslinked.

12. The macrocapsule according to claim 11, wherein the core of each of said microcapsules is covalently crosslinked.

13. The macrocapsule according to claim 4, wherein at least the outer layer of each of said microcapsules is covalently crosslinked.

14. The macrocapsule according to claim 13, wherein the core of each of said microcapsules is covalently crosslinked.

15. The macrocapsule according to claim 5, wherein at least the outer layer of each of said microcapsules is covalently crosslinked.

16. The macrocapsule according to claim 15, wherein the core of each of said microcapsules is covalently crosslinked.

17. The macrocapsule according to claim 6, wherein at least the outer layer of each of said microcapsules is covalently crosslinked.

18. The macrocapsule according to claim 17, wherein the core of each of said microcapsules is covalently crosslinked.

19. A delivery system for biologically active materials comprising a macrocapsule according to claim 1, wherein said biologically active material is selected from the group consisting of living cells, biological materials, pharmacologically active drugs, and diagnostic agents.

20. The delivery system according to claim 19, wherein said biologically active material comprises living cells.

21. The delivery system according to claim 20, wherein said living cells are selected from the group consisting of pancreatic islet cells, tumor cells, human T-lymphoblastoid cells, islet of Langerhans cells, dopamine secreting cells, nerve growth factor cells, hepatocytes, adrenalin/angiotensin secreting cells, parathyroid cells, and norepinephrine/metencephalin secreting cells.

22. The delivery system according to claim 19, wherein said biologically active material comprises biological materials.

23. The delivery system according to claim 19, wherein said biologically active material comprises pharmacologically active drugs.

24. The delivery system according to claim 19, wherein said biologically active material comprises diagnostic agents.

25. The delivery system according to claim 19, wherein said biologically active material comprises pancreatic islet cells.

26. A method of making a macrocapsule containing biologically active materials therein and having substantially no ionic crosslinking in at least the outer layer thereof, said method comprising subjecting an ionically crosslinked macrocapsule which contains biologically active materials therein to conditions sufficient to disrupt the ionic crosslinking in at least the outer layer thereof, wherein:

a macrocapsule is formed having substantially no ionic crosslinking in at least the outer layer thereof, wherein:

said biologically active materials are optionally contained within at least one optionally present microcapsule, wherein:

when microcapsules are not present, at least the outer layer of the macrocapsule is covalently crosslinked and optionally polyionically crosslinked, and when at least one microcapsule is present, at least the outer layer of the macrocapsule is covalently crosslinked or polyionically crosslinked or both covalently crosslinked and polyionically crosslinked.

* * * * *